US011806081B2

(12) United States Patent
Nevins et al.

(10) Patent No.: US 11,806,081 B2
(45) Date of Patent: Nov. 7, 2023

(54) SYSTEM AND METHOD FOR LOCATION DETERMINATION USING MOVEMENT OF AN OPTICAL LABEL FIXED TO A BONE USING A SPATIAL MAPPING CAMERA

(71) Applicants: Russell Todd Nevins, Las Vegas, NV (US); David Jon Backstein, Toronto (CA); Bradley H. Nathan, Toronto (CA)

(72) Inventors: Russell Todd Nevins, Las Vegas, NV (US); David Jon Backstein, Toronto (CA); Bradley H. Nathan, Toronto (CA)

(73) Assignees: Russell Todd Nevins, Las Vegas, NV (US); David Jon Backstein, Toronto (CA); Bradley H. Nathan, Toronto (CA)

( * ) Notice: Subject to any disclaimer, the term of this patent is extended or adjusted under 35 U.S.C. 154(b) by 0 days.

(21) Appl. No.: 17/898,401

(22) Filed: Aug. 29, 2022

(65) Prior Publication Data
US 2022/0409284 A1 Dec. 29, 2022

Related U.S. Application Data

(63) Continuation of application No. 17/686,357, filed on Mar. 3, 2022, which is a continuation of application (Continued)

(51) Int. Cl.
*A61B 5/00* (2006.01)
*A61B 34/10* (2016.01)
(Continued)

(52) U.S. Cl.
CPC .............. *A61B 34/10* (2016.02); *A61B 34/20* (2016.02); *A61B 90/361* (2016.02); *A61B 90/50* (2016.02);
(Continued)

(58) Field of Classification Search
CPC ... A61B 34/10; A61B 34/20; A61B 2034/107; A61B 2034/2065; A61B 2090/363; A61B 2090/365; A61B 2090/502
See application file for complete search history.

(56) References Cited

U.S. PATENT DOCUMENTS 7,331,929 B2  2/2008  Morita et al.
7,812,815 B2  10/2010  Banerjee
(Continued)

FOREIGN PATENT DOCUMENTS

CN  107430437 A  12/2017
CN  110430809 A  11/2019
(Continued)

OTHER PUBLICATIONS

Microsoft HoloLens & Mixed /Reality Healthcare Industry Deck, unknown author, at least as early as Oct. 14, 2019.
(Continued)

*Primary Examiner* — Joel F Brutus
(74) *Attorney, Agent, or Firm* — MORRISS O'BRYANT COMPAGNI CANNON, PLLC

(57) ABSTRACT

A system for determining a location for a surgical procedure, having a 3D spatial mapping camera, the 3D spatial mapping camera configured to map a bone. The system also includes a marker attached to a distal end section of the bone, such that the 3D spatial mapping camera is configured to capture a plurality of images of the marker as the bone is rotated in a non-linear path. The images also include data identifying a location of the marker. The system also includes a computer system that receives the data from the images captured by the 3D spatial mapping camera and determines a location of a mechanical axis of the bone, and a mixed reality display, where the computer system is configured to send the location of the mechanical axis to the mixed reality display and
(Continued)

the mixed reality display is configured to provide a virtual display of the mechanical axis of the bone.

30 Claims, 14 Drawing Sheets

Related U.S. Application Data

No. 17/562,917, filed on Dec. 27, 2021, now abandoned, which is a continuation of application No. 17/402,360, filed on Aug. 13, 2021, now abandoned, which is a continuation of application No. 17/221,760, filed on Apr. 2, 2021, now abandoned.

(51) Int. Cl.
 *A61B 90/00* (2016.01)
 *A61B 90/50* (2016.01)
 *A61B 90/96* (2016.01)
 *A61B 34/20* (2016.01)
 *A61B 90/94* (2016.01)

(52) U.S. Cl.
 CPC .............. *A61B 90/96* (2016.02); *A61B 90/94* (2016.02); *A61B 2034/105* (2016.02); *A61B 2034/107* (2016.02); *A61B 2034/2055* (2016.02); *A61B 2034/2065* (2016.02); *A61B 2090/363* (2016.02); *A61B 2090/365* (2016.02); *A61B 2090/502* (2016.02)

(56) References Cited

U.S. PATENT DOCUMENTS

| | | |
|---|---|---|
| 8,123,754 B2 | 2/2012 | Siebel |
| 8,560,047 B2 | 10/2013 | Haider et al. |
| 8,876,830 B2 | 11/2014 | Hodorek |
| 8,954,181 B2 | 2/2015 | MacLeod |
| 8,956,165 B2 | 2/2015 | Kurenov |
| 9,563,266 B2 | 2/2017 | Banerjee |
| 9,730,713 B2 | 8/2017 | Park |
| 9,861,446 B2 | 1/2018 | Lang |
| 9,892,564 B1 | 2/2018 | Cvetko et al. |
| 9,978,141 B2 | 5/2018 | Stolka et al. |
| 9,980,780 B2 | 5/2018 | Lang |
| 10,016,243 B2 | 7/2018 | Esterberg |
| 10,108,266 B2 | 10/2018 | Banerjee |
| 10,159,530 B2 | 12/2018 | Lang |
| 10,194,990 B2 | 2/2019 | Amanatullah |
| 10,220,181 B2 | 3/2019 | Giap |
| 10,241,569 B2 | 3/2019 | Lanman |
| 10,278,777 B1 | 5/2019 | Lang |
| 10,285,765 B2 | 5/2019 | Sachs |
| 10,286,179 B2 | 5/2019 | Giap |
| 10,292,768 B2 | 5/2019 | Lang |
| 10,368,947 B2 | 8/2019 | Lang |
| 10,401,954 B2 | 9/2019 | Koker |
| 10,405,873 B2 | 9/2019 | Amiot |
| 10,405,927 B1 | 9/2019 | Lang |
| 10,437,335 B2 | 10/2019 | Daniels |
| 10,437,339 B2 | 10/2019 | Banerjee |
| 10,602,114 B2 | 3/2020 | Casas |
| 10,672,288 B2 | 6/2020 | Ribeira et al. |
| 10,716,643 B2 | 7/2020 | Justin et al. |
| 10,888,399 B2 | 1/2021 | Kopelman et al. |
| 10,980,601 B2 | 4/2021 | Yang et al. |
| 11,045,263 B1 | 6/2021 | Nevins et al. |
| 11,172,990 B2 | 11/2021 | Lang |
| 2005/0251030 A1 | 11/2005 | Azar et al. |
| 2008/0183179 A1 | 7/2008 | Siebel |
| 2009/0163923 A1 | 6/2009 | Flett |
| 2012/0046540 A1* | 2/2012 | Branch ................. A61B 5/459 600/407 |
| 2014/0222462 A1 | 8/2014 | Shakil et al. |
| 2014/0272773 A1 | 9/2014 | Merritt et al. |
| 2016/0191887 A1 | 6/2016 | Casas |
| 2016/0261300 A1 | 9/2016 | Fei et al. |
| 2017/0245781 A1 | 8/2017 | Kay |
| 2017/0258526 A1 | 9/2017 | Lang |
| 2017/0312032 A1 | 11/2017 | Amanatullah et al. |
| 2017/0367766 A1 | 12/2017 | Mahfouz |
| 2017/0367771 A1 | 12/2017 | Tako et al. |
| 2018/0049622 A1 | 2/2018 | Ryan et al. |
| 2018/0090029 A1 | 3/2018 | Fisher |
| 2018/0098813 A1 | 4/2018 | Nesichi |
| 2018/0116728 A1 | 5/2018 | Lang |
| 2018/0168740 A1* | 6/2018 | Ryan ...................... A61B 90/36 |
| 2018/0185100 A1* | 7/2018 | Weinstein ............... A61F 2/461 |
| 2018/0240276 A1 | 8/2018 | He et al. |
| 2018/0348876 A1 | 12/2018 | Banerjee |
| 2019/0038362 A1 | 2/2019 | Nash et al. |
| 2019/0076198 A1 | 3/2019 | Berend |
| 2019/0110842 A1 | 4/2019 | Lang |
| 2019/0142520 A1 | 5/2019 | VanDyken |
| 2019/0149797 A1 | 5/2019 | Casas |
| 2019/0216562 A1 | 7/2019 | Sachs |
| 2019/0262078 A1 | 8/2019 | Lang |
| 2019/0366030 A1 | 12/2019 | Giap et al. |
| 2019/0369717 A1 | 12/2019 | Frielinghaus et al. |
| 2019/0380792 A1 | 12/2019 | Poltaretskyi et al. |
| 2020/0000527 A1 | 1/2020 | Cazal |
| 2020/0037043 A1 | 1/2020 | Phillips et al. |
| 2020/0078100 A1 | 3/2020 | Weinstein et al. |
| 2020/0107003 A1 | 4/2020 | Phillips et al. |
| 2020/0275976 A1 | 9/2020 | McKinnon |
| 2020/0275988 A1 | 9/2020 | Johnson et al. |
| 2020/0302694 A1 | 9/2020 | Flexman et al. |
| 2020/0360093 A1 | 11/2020 | Khan et al. |
| 2020/0375666 A1 | 12/2020 | Murphy |
| 2021/0088811 A1 | 3/2021 | Varady et al. |
| 2021/0093329 A1 | 4/2021 | Poltaretskyi et al. |
| 2021/0093333 A1 | 4/2021 | Chappuis et al. |
| 2021/0093391 A1 | 4/2021 | Poltaretskyi et al. |
| 2021/0093413 A1 | 4/2021 | Poltaretskyi et al. |
| 2021/0142508 A1 | 5/2021 | Azimi et al. |
| 2021/0228286 A1 | 7/2021 | Moghaddam et al. |
| 2021/0228308 A1 | 7/2021 | Berger et al. |
| 2021/0244481 A1 | 8/2021 | Jaramaz et al. |
| 2022/0047279 A1 | 2/2022 | Nevins et al. |
| 2022/0051483 A1 | 2/2022 | Nevins et al. |

FOREIGN PATENT DOCUMENTS

| | | |
|---|---|---|
| CN | 110431636 A | 11/2019 |
| DE | 10103922 A1 | 8/2002 |
| DE | 102015212352 A1 | 1/2017 |
| EP | 3113682 A1 | 1/2017 |
| GB | 2570758 A | 7/2019 |
| JP | 2020515891 A | 5/2020 |
| WO | 2007108776 A2 | 9/2007 |
| WO | 2012033739 A2 | 3/2012 |
| WO | 2015134953 A1 | 9/2015 |
| WO | 2017066373 A1 | 4/2017 |
| WO | 2018007091 A1 | 1/2018 |
| WO | 2018132804 A1 | 7/2018 |
| WO | 2018175971 A1 | 9/2018 |
| WO | 2019051080 A1 | 3/2019 |
| WO | 2019245870 A1 | 12/2019 |
| WO | 2020033568 A2 | 2/2020 |
| WO | 2020037308 A1 | 2/2020 |
| WO | 2020047051 A1 | 3/2020 |
| WO | 2020145826 A1 | 7/2020 |
| WO | 2021094354 A1 | 5/2021 |

OTHER PUBLICATIONS

Kaluschke et al., HIPS—A Virtual Reality Hip Prosthesis Implantation Simulator, retrieved at https://www.reasearchgate.net/publication/327329265, upload date Sep. 3, 2018 DOI: 10.1109/VR.2018.8446370.

Vaughan et al., Does Virtual-Reality Training on Orthopaedic Simulators Improve Performance in the Operating Room? Science and

(56) References Cited

OTHER PUBLICATIONS

Information Conference 2015, Jul. 28-30, 2015, London, UK; retrieved at https://www.researchgate.net/publication/284415791; DOI: 10.1109/SAI.2015.7237125.

Patently Apple—Apple Reveals a Mixed Reality Headset that Uses a Direct Retinal Projector System With Holographic Lenses, retrieved at https://www.patentlyapple.com/patently-apple/2019/09/apple-reveals-a-mixed-reality-headset-that-uses-a-direct-retinal-projector-system-with-hologra . . . , posted date Sep. 19, 2019.

Virtual Reality System Helps Surgeons, Reassures Patients, retrieved at https//medicalgiving.stanford.edu/news/virtual-reality-system-helps-surgeons-reassures-patients.html, retrieved date Oct. 24, 2019.

Immersive Touch Launches the First Virtual Reality Integrated Suite for Surgical Planning, retrieved at https://spinalnewsinternational.com/immersivetouch-virtual-reality-suite, dated Oct. 5, 2018.

Daley, Sam, The Cutting Edge: 10 Companies Bringing Virtual Reality & AR to the OR, retrieved at https://builtin.com/healthcare-technology/augmented-virtual-reality-surgery, dated Jul. 5, 2019.

Barad, Justin, Virtual and Augmented Reality Can Save Lives by Improving Surgeons' Training, retrieved at https://www.statnews.com/2019/08/16/virtual-reality-improve-surgeon-training, dated Aug. 16, 2019.

Levin et al., The Future of Virtual Reality in Ophthalmology Is Already Here, retrieved at https://www.aao.org/young-ophthalmologists/yo-info/article/future-of-virtual-reality-in-ophthalmology, dated Aug. 16, 2019.

Vaughan et al., A Review of Virtual Reality Based Training Simulators for Orthopaedic Surgery, retrieved at https://www.researchgate.net/publication/283727217, posted date Feb. 22, 2019, DOI: 10.1016/j.medengphy.2015.11.021.

LexInnova Patent Landscape Analysis, Virtual Reality, unknown author, copyright date of 2015.

Virtual & Augmented Reality Are You Sure it Isn't Real? Kathleen Boyle, CFA, Managing Editor, Citi GPS dated Oct. 2016.

New Apple patent filing shows a mixed reality headset that tracks your whole face, Jul. 22, 2019, (downloaded Jul. 1, 2020 at https://www.theverge.com/2019/7/22/20705158/apple-mixed-reality-headset-ar-glasses-patent-application-face-tracking), 2 pages.

"Augmented and virtual reality in surgery—the digital surgical environment: application, limitations and legal pitfalls," accessed at https://www.ncbi.nlm.nih.gov/pmc/articles/PMC5220044/, visited on Jul. 4, 2020. 12 pages.

"The impact of Web3D technologies on medical education and training," Science Direct, accessed at https://www.sciencedirect.com/science/article/pii/S0360131505000825, visited on Jul. 4, 2020, 11 pages.

"Mixed Reality with HoloLens: Where Virtual Reality Meets Augmented Reality in the Operating Room," accessed at https://www.ingentaconnect.com/content/wk/prs/2017/00000140/00000005/art00063, visited on Jul. 4, 2020, 1 page.

"Virtual Reality Simulation in Neurosurgery: Technologies and Evolution," Abstract, accessed at https://academic.oup.com/neurosurgery/article-abstract/72/suppL_1/A154/2417686, visited on Jul. 4, 2020, 2 pages.

Katanacho, Manuel, Wladimir De la Cadena, and Sebastian Engel. "Surgical navigation with QR codes: Marker detection and pose estimation of QR code markers for surgical navigation." Current Directions in Biomedical Engineering 2.1 (2016): 355-358.

* cited by examiner

SYSTEM AND METHOD FOR LOCATION DETERMINATION USING MOVEMENT OF AN OPTICAL LABEL FIXED TO A BONE USING A SPATIAL MAPPING CAMERA

CROSS-REFERENCE TO RELATED APPLICATIONS

This application is a continuation of U.S. patent application Ser. No. 17/686,357, filed on Mar. 3, 2022, which is a continuation of U.S. patent application Ser. No. 17/562,917, filed on Dec. 27, 2021, which is a continuation of U.S. patent application Ser. No. 17/402,360, filed on Aug. 13, 2021, which is a continuation of U.S. patent application Ser. No. 17/221,760, filed on Apr. 2, 2021, which are hereby incorporated by reference herein in their entirety, including but not limited to those portions that specifically appear hereinafter, the incorporation by reference being made with the following exception: in the event that any portion of the above-referenced applications is inconsistent with this application, this application superseded said above-referenced applications.

STATEMENT REGARDING FEDERALLY SPONSORED RESEARCH OR DEVELOPMENT

Not applicable.

BACKGROUND

1. The Field of the Present Disclosure

The present disclosure relates generally to surgical systems and methods of facilitating the efficiency and accuracy of implanting surgical prostheses using fixed markers attached to an end portion of a bone, mixed reality and 3D spatial mapping devices.

2. Description of Related Art

In conventional knee replacement procedures, a femur is cut on a distal end which can then receive a knee replacement. Conventionally, an anatomical axis of the femur is identified by inserting a rod into the femoral canal of the femur. The rod is inserted into the entire length of the femur and acts as an identifier for the anatomical axis of the femur. A mechanical axis of the femur can be estimated as shifted at about 5 degrees, or 5 degrees offset, from the anatomical axis of the rod. A cut line, or cut plane, is then identified as perpendicular to the mechanical axis. The mechanical axis is conventionally difficult to identify in the operating room because of the engagement of the proximal end of the femur in the hip socket. However, this conventional procedure, inserting a rod into the entire length of the femur, is very invasive, which can cause a variety of complications and potential injury to the patient.

Once the mechanical axis is identified, the proper positioning of a jig or knee implant can be made. A femoral implant and tibial implant are typically designed to be surgically implanted into the distal end of the femur and the proximal end of the tibia, respectively. The femoral implant is further designed to cooperate with the tibial implant in simulating the articulating motion of an anatomical knee joint.

These femoral and tibial implants, in combination with ligaments and muscles, attempt to duplicate natural knee motion as well as absorb and control forces generated during the range of flexion. In some instances however, it may be necessary to replace or modify an existing femoral and/or tibial implant. Such replacements are generally referred to as revision implants.

To prepare a femur and tibia for such a knee replacement and form an engagement with femoral and tibial implants, the femur and tibia bones must be cut in very specific and precise ways and at very specific and precise angles and locations, so that the prepared bone will properly engage with and be secured to the corresponding implants. In order to make these cuts properly, a surgeon traditionally uses a jig, or surgical cutting guide as known to those skilled in the field, which can be removably attached or secured to the bone, such that slots, or guides, in the jig facilitate the precise cuts necessary to secure the corresponding implants.

The phrase "jig" as used herein, shall thus refer broadly to a surgical cutting guide, that may be configured and arranged to be fixed or attached to a bone, or may be secured adjacent to a bone or other tissue to be cut by a surgeon and identify a relative location, angle and/or cutting plane that a surgeon should cut on the adjacent bone or tissue, as known in the art. A jig may include predetermined slots and/or cutting surfaces to identify where a surgeon should cut the adjacent bone or tissue, wherein such cuts may correspond to a shape of a surgical implant that may be attached to the cut bone or tissue.

Therefore, there is a need for a system that can identify a mechanical axis of the femur, or the center of the femoral head, without having to insert a rod into the femur or expose the hip socket, which can lead to complication during surgery and require significant surgery time and additional recovery time for the patient.

Accordingly, there is a need for a system and method of utilizing a virtual or holographic mechanical axis or surgical instrument that could facilitate increased accuracy and precision of required or desired bone cuts.

The phrases "virtual jig," "holographic jig," "virtual axis," or "holographic axis" as used herein, shall thus refer broadly to any visual rendering or projection representing an actual physical jig, or mechanical or anatomical axis of a bone, as the case may be, having some, all, or mostly all, of the same visual characteristics of the physical jig or axis, as the case may be, including the visual appearance of the same size and shape as the physical objects being virtually represented, as known in the art.

The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims. Any discussion of documents, acts, materials, devices, articles or the like which has been included in the present specification is not to be taken as an admission that any or all of these matters form part of the prior art base, or were common general knowledge in the field relevant to the present disclosure as it existed before the priority date of each claim of this application.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1A:
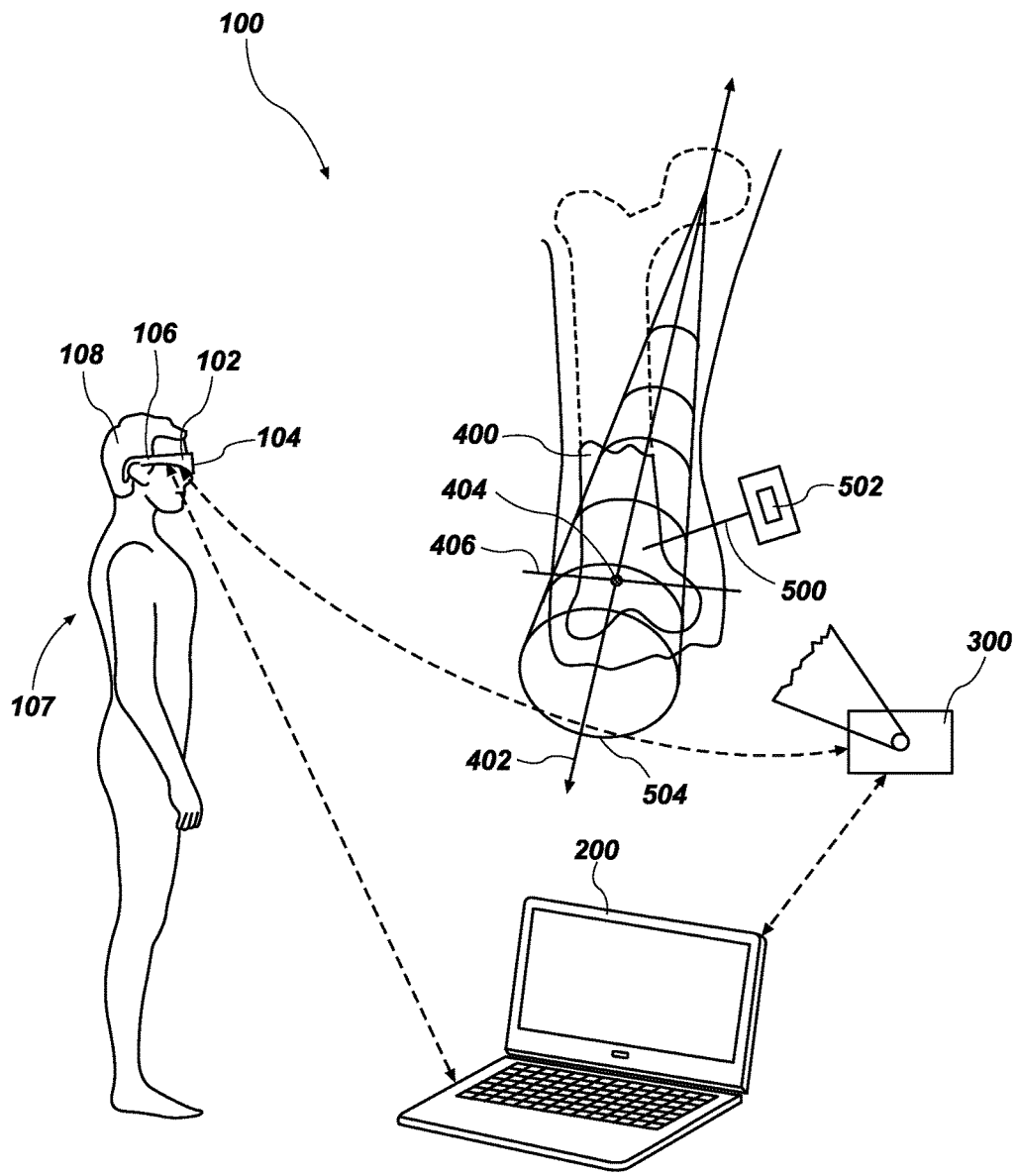
FIG. 1a is a schematic rendering of a mixed reality system of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," including," "containing," "characterized by," and grammatical equivalents thereof are inclusive or open-ended terms that do not exclude additional, unrecited elements or method steps.

As used herein, the terms "virtual" and "hologram" are used interchangeably, and grammatical equivalents thereof are inclusive or open-ended terms that do not exclude additional, unrecited elements or method steps. These terms are used to describe visual representations of an actual physical object, device or element, having some, all, or mostly all, of the same visual characteristics of the physical device, including the visual appearance of the same size and shape as the physical object device or element being virtually represented.

Applicant has discovered a novel system and method for generating and using a virtual axis and/or virtual instrument, in a surgical procedure, for example, in a knee or tibial implant procedure, or other desired surgical procedure.

The phrase "virtual system" as used herein, shall refer broadly to any system capable of generating or creating a simulated or virtual rendering or projection of physical or structural objects, devices or features virtually identical or, substantially identical to an actual physical device, object, instrument or other structure, as known in the art. A virtual system may also include a device, mechanism, or instrument capable of projecting or displaying the desired simulated or virtual rendering or projection of physical or structural features virtually identical or substantially identical to an actual physical device or features or portions thereof. A virtual system may also enable a user to manipulate, move and/or modify the simulated or virtual rendering or projection.

The phrase "mixed or augmented reality system" as used herein, shall refer broadly to any system capable of generating or creating a simulated or virtual rendering or projection of physical or structural objects, devices or features virtually identical or substantially identical to an actual physical device, instrument or other structure or feature or portions thereof, as known in the art. A mixed or augmented reality system may also include a device, mechanism, or instrument capable of projecting or displaying the desired a simulated or virtual rendering or projection of physical or structural features virtually identical or substantially identical to an actual physical device overlaid or concurrently with actual physical structures, objects, mechanisms or devices in reality, thus incorporating the virtual rendering or projection in real world settings with actual physical elements. A mixed or augmented reality system may also enable a user to manipulate, move and/or modify the simulated or virtual rendering or projection.

The phrase "mixed or augmented reality instrument" as used herein, shall refer broadly to any device, mechanism or instrument used in a mixed or augmented reality system, including a device capable of generating or creating a simulated or virtual rendering or projection of physical or structural elements and/or features virtually identical or substantially identical to an actual physical device, object, instrument or other physical structure, as known in the art. A mixed or augmented reality instrument may also be capable of projecting or displaying the desired simulated or virtual rendering or projection of physical or structural features or elements virtually identical or substantially identical to an actual physical device or object overlaid or concurrently with actual physical structures, object, mechanism or devices in reality, thus incorporating the virtual rendering or projection in real world settings with actual physical elements or features. A mixed or augmented reality instrument may also enable a user to manipulate, move and/or modify the simulated or virtual rendering or projection.

The phrase "holographic representation" as used herein, shall refer broadly to a visual rendering or projection representing an actual physical device, object or element or portion thereof, having some, all, or mostly all, of the same visual characteristics of the corresponding physical device, object or element, including the visual appearance of the same size and shape as the physical objects being virtually represented, as known in the art.

Referring to the drawings, where like numbers represent like elements, FIG. 1a, in a disclosed embodiment, illustrates a mixed or augmented reality system, generally indicated at 100, which can be used to produce, or display, a desired mixed or augmented reality instrument, such as an anatomical or mechanical axis of a bone in a display to a surgeon or user, or stated another way, that is visible and manipulatable by a surgeon or user. The mixed or augmented reality system 100 may also enable a user to activate or deactivate, in full or in part, the marker, such as an axis, or virtual instrument(s), making a virtual axis appear or disappear, as desired in a mixed reality assisted surgery, for example.

The mixed or augmented reality system 100 may include a mixed or augmented reality headset 102 which may include a transparent or mostly transparent viewer 104, or display, which can be suspended or positioned in front of a user's eyes. In alternative embodiments, the viewer 104, or mixed reality display, may be a stand-alone device detached and separate from the surgeon, or may be mounted in another desired location in an operating room or other desired location. The headset 102 may include a headband 106 attached to the viewer 104, which may be used to secure the headset 102 to a user's head 108, thereby securing the viewer 104 in place in front of the user's eyes.

The transparent viewer 104 may be configured to project, or otherwise make viewable, on an interior surface of the viewer 104, a holographic virtual image or images, such as a virtual instrument, for example, an anatomical or mechanical axis of a bone, which may be positionally manipulated by the user, surgeon, third party or remote system, such as a remote computer system. For the purpose of this disclosure the term "mechanical axis" as used herein shall be defined broadly in reference to a bone having a proximal joint and a distal joint, as a straight line connecting the joint center points of the proximal and distal joints in the frontal or sagittal planes. The headset 102 may be configured to view holographic images or, alternatively, the holographic images may be turned off and the user wearing the headset 102 may be able to view the surrounding environment through the transparent viewer 104, unobstructed. As such, a user, such as a surgeon for example, can wear the mixed or augmented reality headset 102 and then can choose to activate a holographic image to aide in facilitating a surgical procedure and then shut off the holographic image in order to perform the surgical procedure un-obscured, visually.

One embodiment of the disclosed headset 102 may be a product created and manufactured by Microsoft, known as the HaloLens® mixed or augmented reality system, or any suitable mixed or augmented reality system for generating virtual images viewable by a user or surgeon. Headset 102 may be a conventional "off the shelf" product with a built-in platform that enables all of the features described herein with respect to the headset 102.

In addition to identifying axes of a bone, in alternative embodiments, the headset 102, such as a Microsoft HoloLens product, can be loaded or preloaded with all desired or required virtual instruments, including virtual jigs or surgical cutting guides, virtual drill bits, and/or a virtual target which can identify relative locations of a plurality of holes to be drilled by a surgeon to facilitate the fastening of a jig or other device onto a desired bone at the proper desired location, and any other desired virtual instruments or holograms. The Microsoft HoloLens product and its capabilities and features, or any suitable mixed or augmented reality system such as is described herein with respect to the headset 102, are known to those skilled in the art.

The mixed reality system 100 may also include a computer or computer system 200 having enabling software to communicate with the headset 102, by both receiving information from the headset 102 and transmitting data and virtual images to the headset 102. It is therefore to be understood, by way of the circuit diagram and dashed lines shown in FIG. 1, that headset 102 is electronically connected to the computer system 200 and a 3D spatial mapping device or camera 300. The 3D spatial mapping camera 300 is electronically connected to the headset 102 and the computer system 200, as represented by the dashed lines shown in FIG. 1. While the 3D spatial mapping camera 300 is electronically connected to the headset 102, the 3D spatial mapping camera 300 may be separate from and not mechanically connected to the headset 102.

The mixed reality system 100 may also include a 3D spatial mapping camera 300. One embodiment of the disclosed spatial mapping camera 300 may be a product created and manufactured by Microsoft, known as the Azure Kinect®, or any suitable 3D spatial mapping camera or LiDAR Scanner capable of continuous 3D mapping and transition corresponding 3D images, such as bones, anatomy, or other desired 3D objects. The spatial mapping camera 300 may be a conventional "off the shelf" product with a built-in platform that enables all of the features described herein with respect to the spatial mapping camera 200. Furthermore, the spatial mapping camera 200, such as a Microsoft Azure Kinect product, can be loaded or preloaded with all necessary software to enable wireless communication between the spatial mapping camera 300 and the computer system 200 and/or the headset 102. The Microsoft Azure Kinect product and its capabilities and features, or any suitable 3D spatial mapping camera such as is described herein with respect to the spatial mapping camera 300, are known to those skilled in the art.

The headset 102, computer system 200 and spatial mapping camera 300, may be programmed and configured to enable a surgeon 107 to see and manipulate a virtual, or holographic target or axis, with respect a patient's bone 400, anatomical, or any other desired location, which may receive a surgical implant. The headset 102, computer system 200 and spatial mapping camera 300 may communicate with one another via a local network connection, W-Fi, Bluetooth® wireless technology, or any other known wireless communication signal.

Specifically, the spatial mapping camera 300, that may be programed to communicate with the computer system 200 having enabling software, may utilize such enabling software to map the bone 400 and generate map data representative of a three dimensional map of a surface of the bone 400, or other desired anatomy, to help identify the location and orientation of an anatomical or mechanical axis of a bone, which can then facilitate the proper placement of a jig, implant or other device, to the bone 400, prior to cutting the knee.

The mixed reality system 100 may also include a marker 500. The marker 500 may be attached or otherwise fixed to a distal end of the bone 400, which may be exposed. While a plurality of markers 500 may be used, if desired, a single, exclusive marker 500, may also be used in this disclosed embodiment. Bone 400 is a femur in the illustrated embodiment of FIG. 1, however, the marker 500 may be fixed to any desired bone having in inaccessible pivot point or fulcrum. The "distal end section or portion" may include the terminal distal end, the distal end section or portion as used herein being defined broadly as a distal half of the bone 400. The marker 500 may include a scannable, visual, optical label 502, such as a QR code.

The surgeon may attach the marker 500 to an exposed distal end section of the bone 400, at a predetermined or desired location. The spatial mapping camera 300 may spatially map the marker 500 and the exposed bone 400 to map the surface of the exposed bone and relative location of the marker 500, including the optical label 502.

The optical label 502 may include a QR code or other optical identifiers, such as shapes having distinct corners, which can be identified by the 3D spatial mapping camera 300 and the location of the optical label identified and stored.

The surgeon may then rotate the bone 400, with the marker 500 fixed there to, in a non-liner path 504, such as a circular path, ovular path or another desired, predetermined, or random non-liner path. The bone 400 may be rotated about a fulcrum or pivot point that is not exposed to the surgeon's view, for example the socket joint of the hip, but may also include any desired pivot point or fulcrum that may not be exposed to the surgeon, such as a shoulder joint, for example.

At specific time intervals, the 3D spatial mapping camera 300 may capture an image of the location of the marker 500 and optical label 502 and store the location data. The time intervals between the plurality of captures of the location data may be predetermined and consistent time intervals, at random time intervals, or at time intervals controlled by the surgeon. Additionally, the number of image captures by the 3D spatial mapping camera may be set at a predetermined number, or at a random number, or at a number that is determined by the surgeon. For example, the 3D spatial mapping camera may capture an image every second for 30 seconds, or may capture 10 images every second for 3 seconds, or any other desired number of images over any desired time intervals.

After the plurality of image captures of the marker 500 and optical label 502, the images and location data may be sent to the computer system 20 which may then process the image and location data, and using a preloaded algorithm, may generate the mechanical axis 402 of the bone 400.

Additionally, the computer system 200, may also process the image and location data, and using a preloaded algorithm, may generate a mechanical center 404 of the femoral head of the bone 400.

The computer system 200, may also process the image and location data, and using a preloaded algorithm, may generate a cut line 406, or cut plane, that can be used by a surgeon to identify where the bone 400 should be cut in preparation of the attachment of an implant or other desired surgical device. The cut plane 406 forms an angle with the mechanical axis 402 of the bone 400 and may, for example, be oriented orthogonal to the mechanical axis of the bone.

The computer system 200 may then send data related to the mechanical axis 402, mechanical center 404, cutting line or plane 406, and/or virtual jig 410, to the headset 102, which can then utilize the data provided by the computer to provide a virtual image of the mechanical axis 402, mechanical center 404, the cutting line or plane 406, and/or virtual jig 410, relative to the bone 400, which can then be displayed on the viewer 104, that visually appears to overlay bone 400 at a position and in an orientation of the mechanical axis 402 when viewed with the mixed reality display. The surgeon can then view the virtual mechanical axis 402, mechanical center 404, the cutting line or plane 406, and/or virtual jig 410, in their accurate location with respect to the physical bone 400, which can be seen simultaneously with the virtual images. The surgeon can then cut the bone 400, attach a device or implant to the bone 400 or otherwise manipulate the bone using the accurately displayed virtual mechanical axis 402, mechanical center 404, and/or the cutting line or plane 406.

Figure 1B:
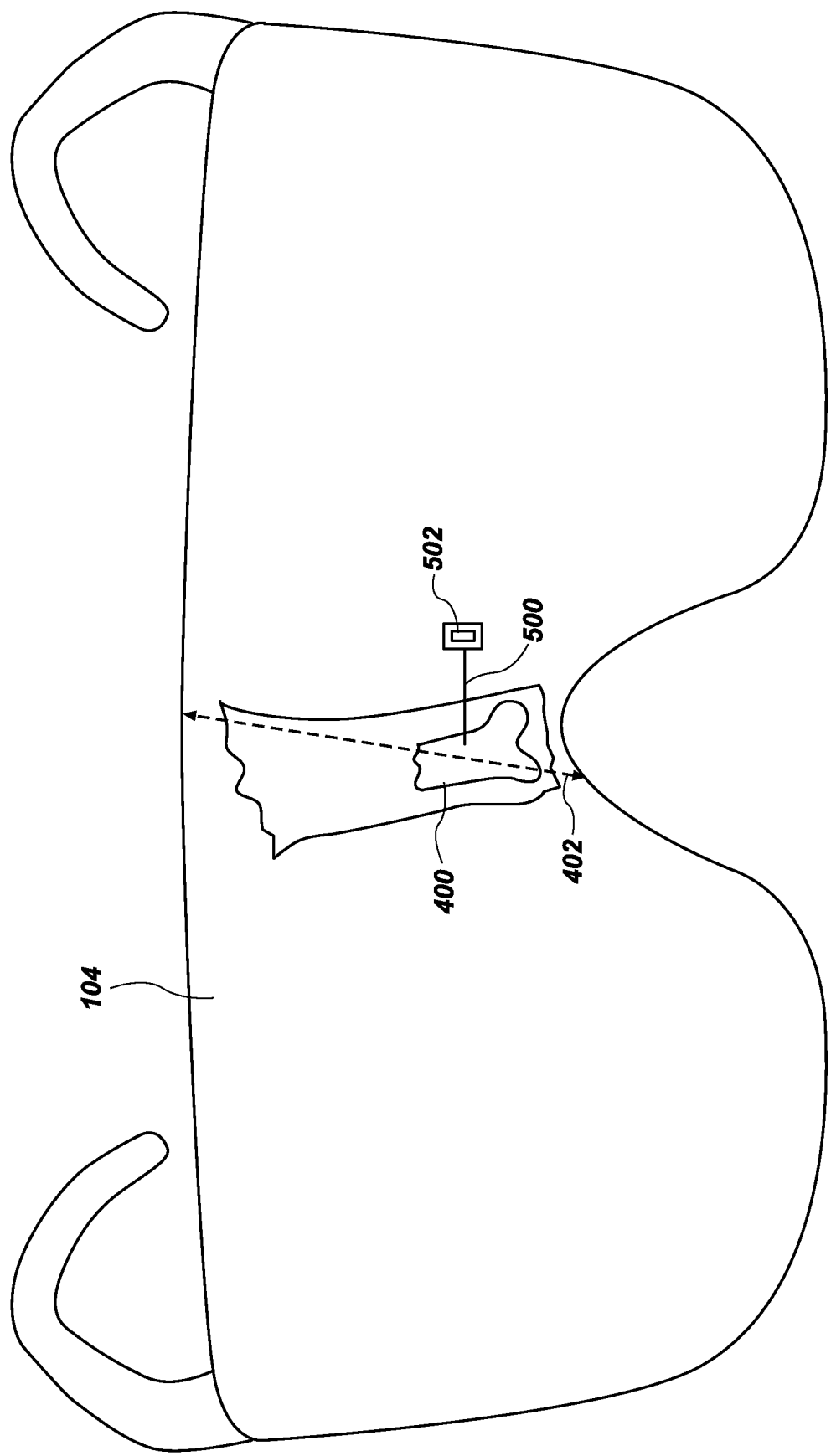
FIG. 1b is a schematic rendering of a view through a mixed reality display of an embodiment of the present disclosure.

FIG. 1b illustrates a schematic view of a perspective through the viewer 104 of the mixed reality headset 102, representing the view of a wearer of the mixed reality headset 100 during a procedure. As shown, the view can display a virtual mechanical axis 402 overlaid on the actual physical bone 400, enabling the wearer to see or view the virtual mechanical axis 402 simultaneously with the bone 400, marker 500 and label 502.

Figure 1C:
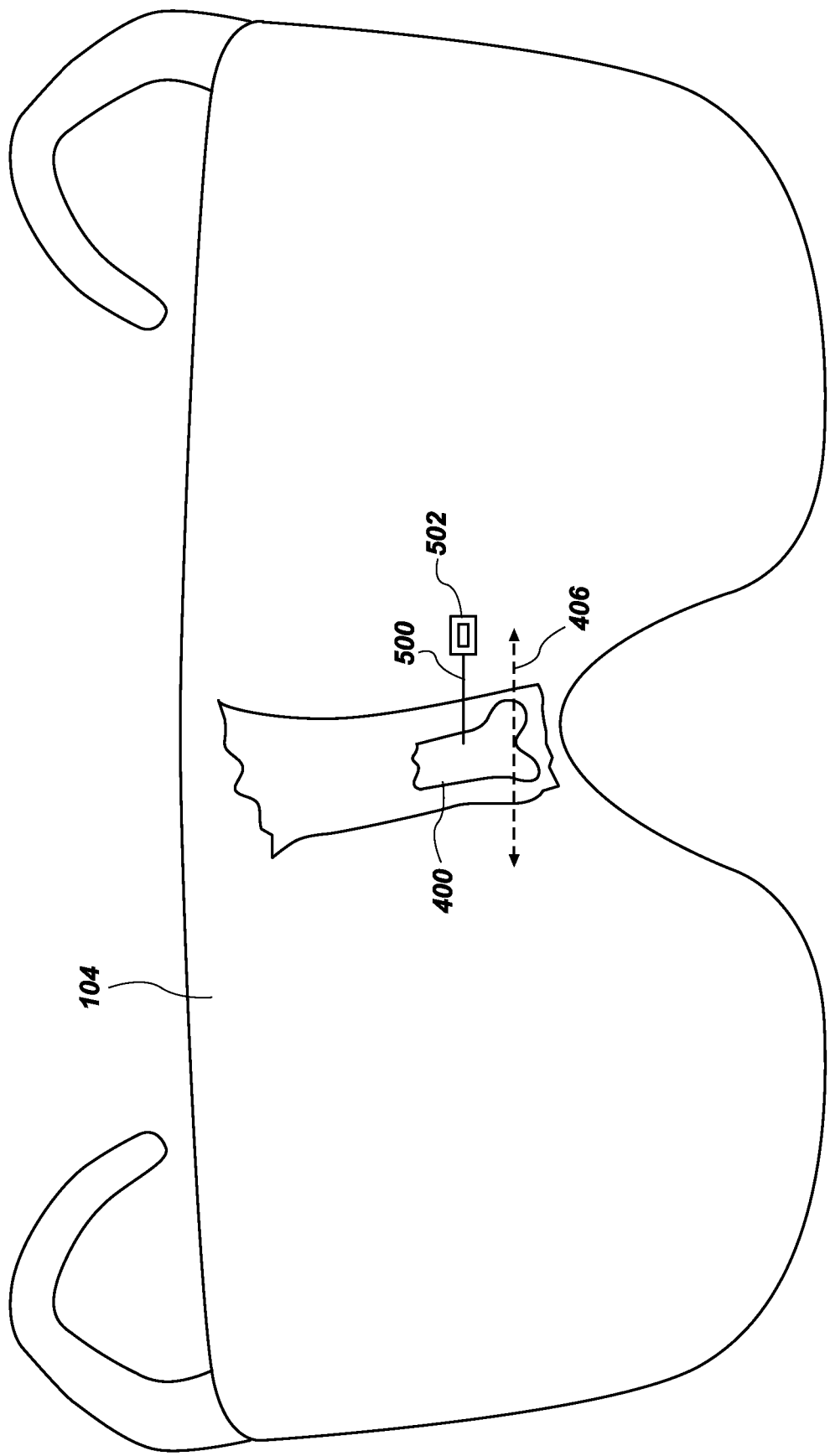
FIG. 1c is a schematic rendering of a view through a mixed reality display of another embodiment of the present disclosure.

FIG. 1c illustrates a schematic view of a perspective through the viewer 104 of the mixed reality headset 102, representing the view of a wearer of the mixed reality headset 100 during a procedure. As shown, the view can display a virtual mechanical axis 402 overlaid on the actual physical bone 400, enabling the wearer to see or view the virtual cutting line or plane 406 simultaneously with the bone 400, marker 500 and label 502.

Figure 1D:
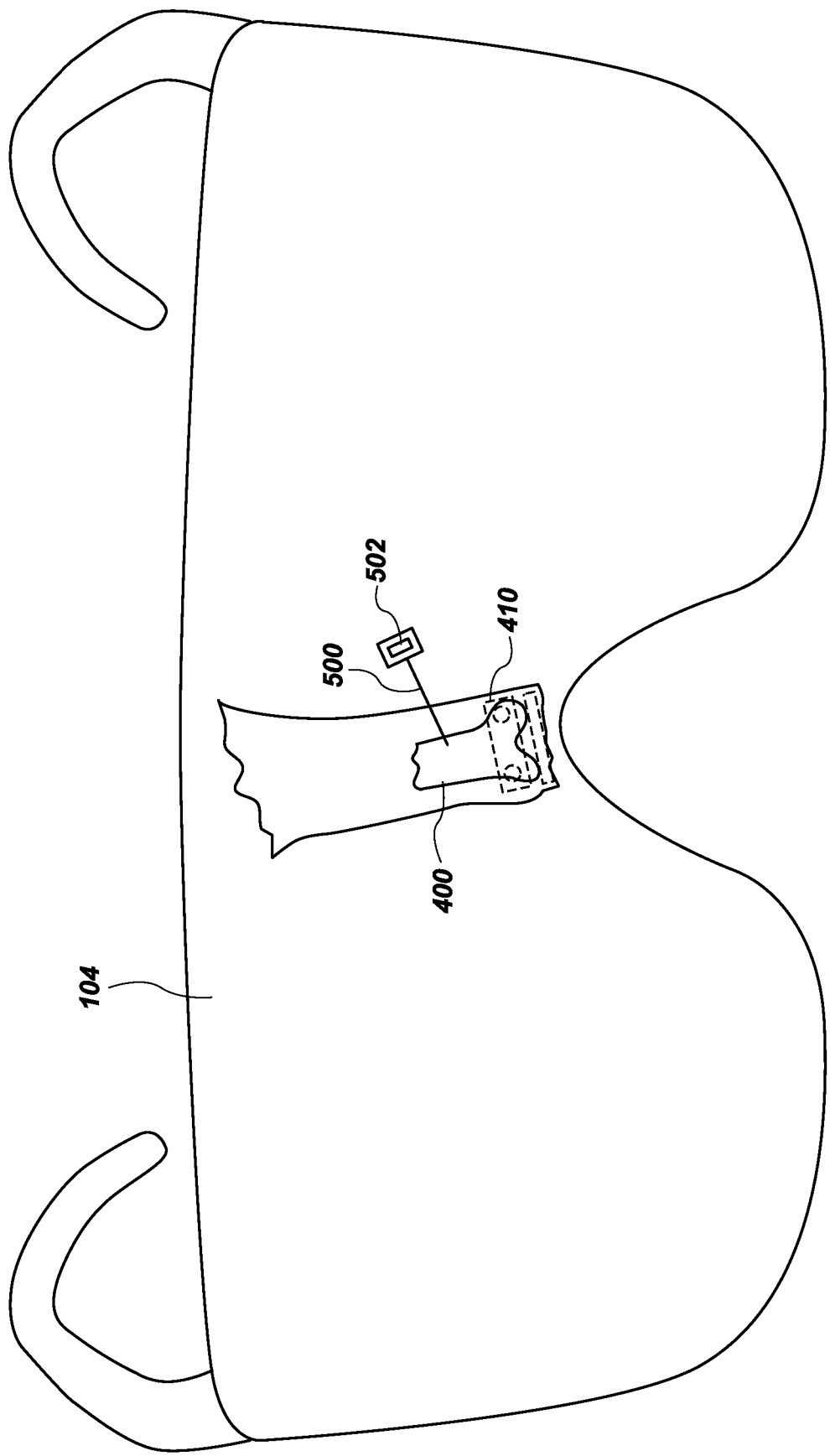
FIG. 1d is a schematic rendering of a view through a mixed reality display of a further embodiment of the present disclosure.

FIG. 1d illustrates a schematic view of a perspective through the viewer 104 of the mixed reality headset 102, representing the view of a wearer of the mixed reality headset 100 during a procedure. As shown, the view can display a virtual mechanical axis 402 overlaid on the actual physical bone 400, enabling the wearer to see or view a virtual jig 410 simultaneously with the bone 400, marker 500 and label 502.

Figure 2:
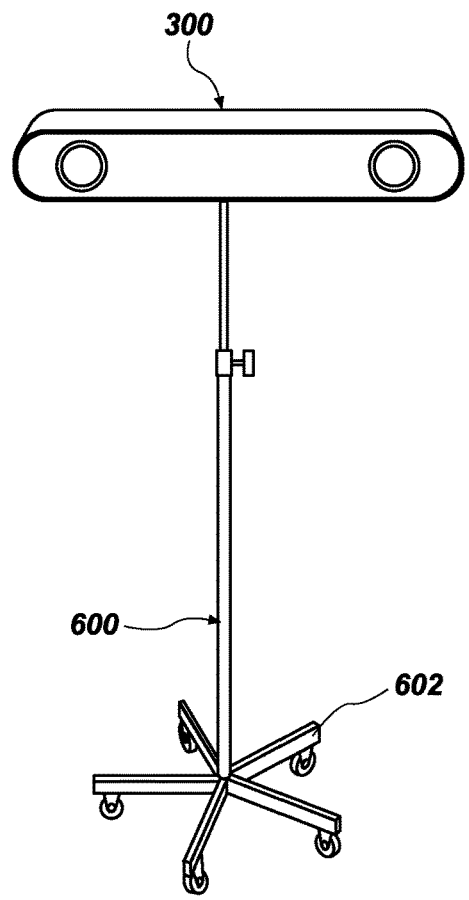
FIG. 2 is a perspective view of a 3D spatial mapping camera of another embodiment of the present disclosure.

In another embodiment, as shown in FIG. 2, the 3D spatial mapping camera may be fixed or removably attached to a stand 600. The stand 600 may be anchored or fixed to a desired location in the operating room, or the stand may be mobile, utilizing a plurality of wheels 602, for example.

Figure 3:
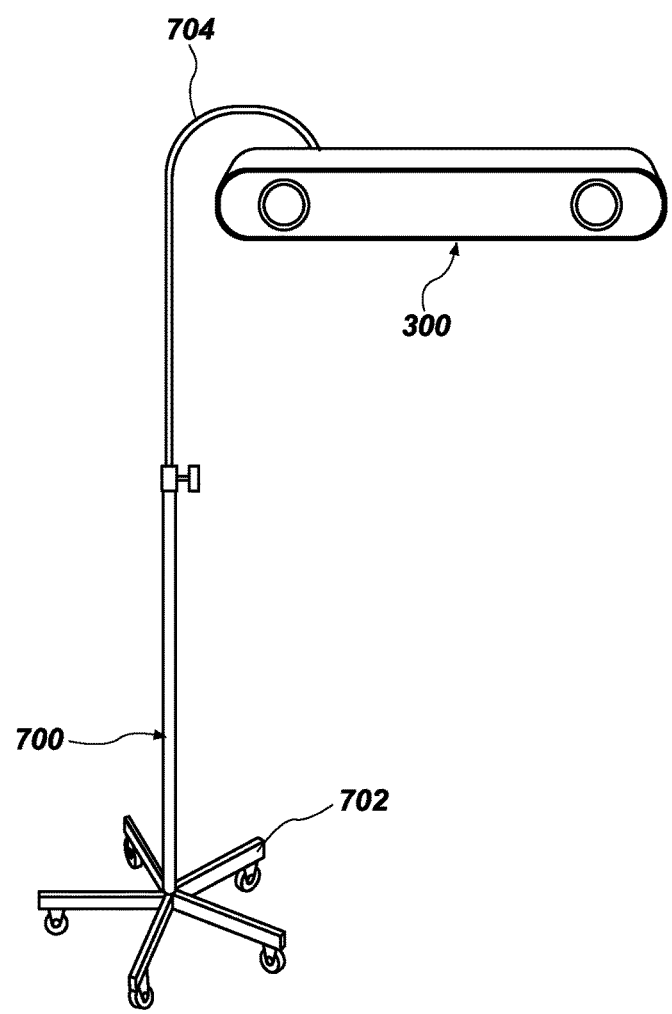
FIG. 3 is a perspective view of a 3D spatial mapping camera of another embodiment of the present disclosure.

In another embodiment, as shown in FIG. 3, the 3D spatial mapping camera 300 may be fixed or removably attached to a stand 700. The stand 700 may be anchored or fixed to a desired location in the operating room, or the stand may be mobile, utilizing a plurality of wheels 702, for example. The stand 700 may also include a flexible arm 704 that may allow a user to manipulate the positioning of the 3D spatial mapping camera 300.

Figure 4:
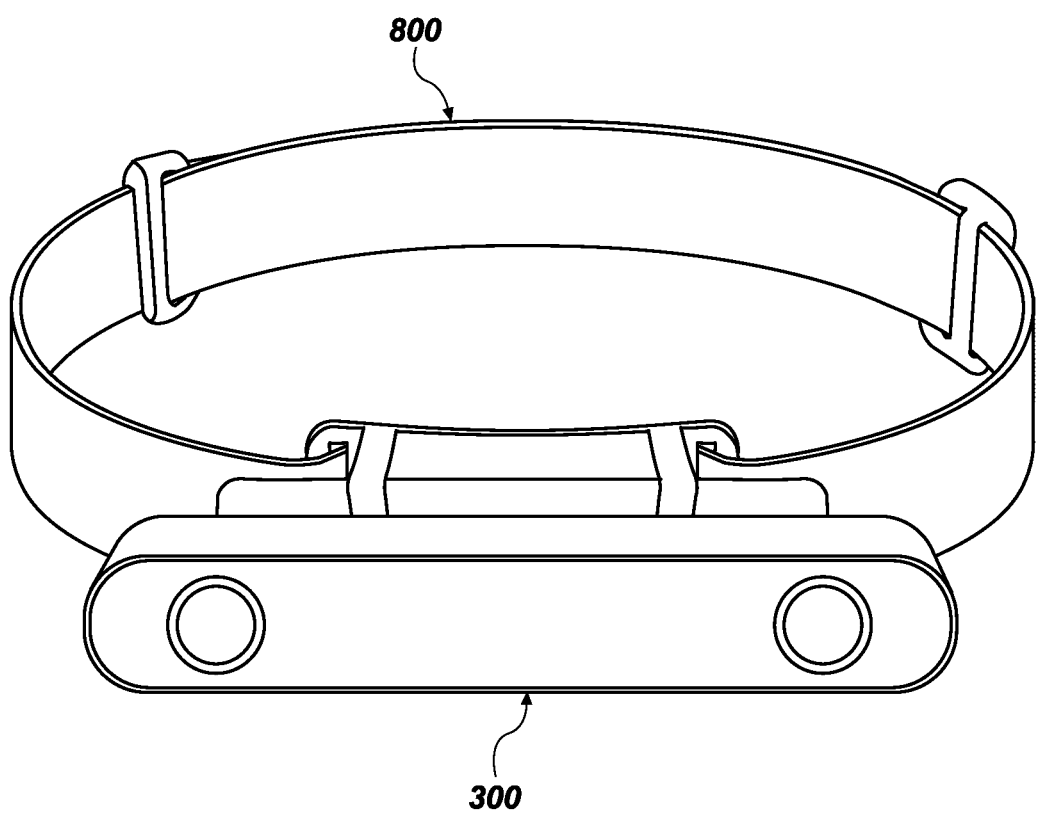
FIG. 4 is a perspective view of a 3D spatial mapping camera of another embodiment of the present disclosure.

In another embodiment, as shown in FIG. 4, the 3D spatial mapping camera 300 may be sized and configured to be fixed or removably attached to a strap 800. The strap 800 may be adjustable and can be configured to be worn by a user around their head, chest or other desired part of the body.

Figure 5:
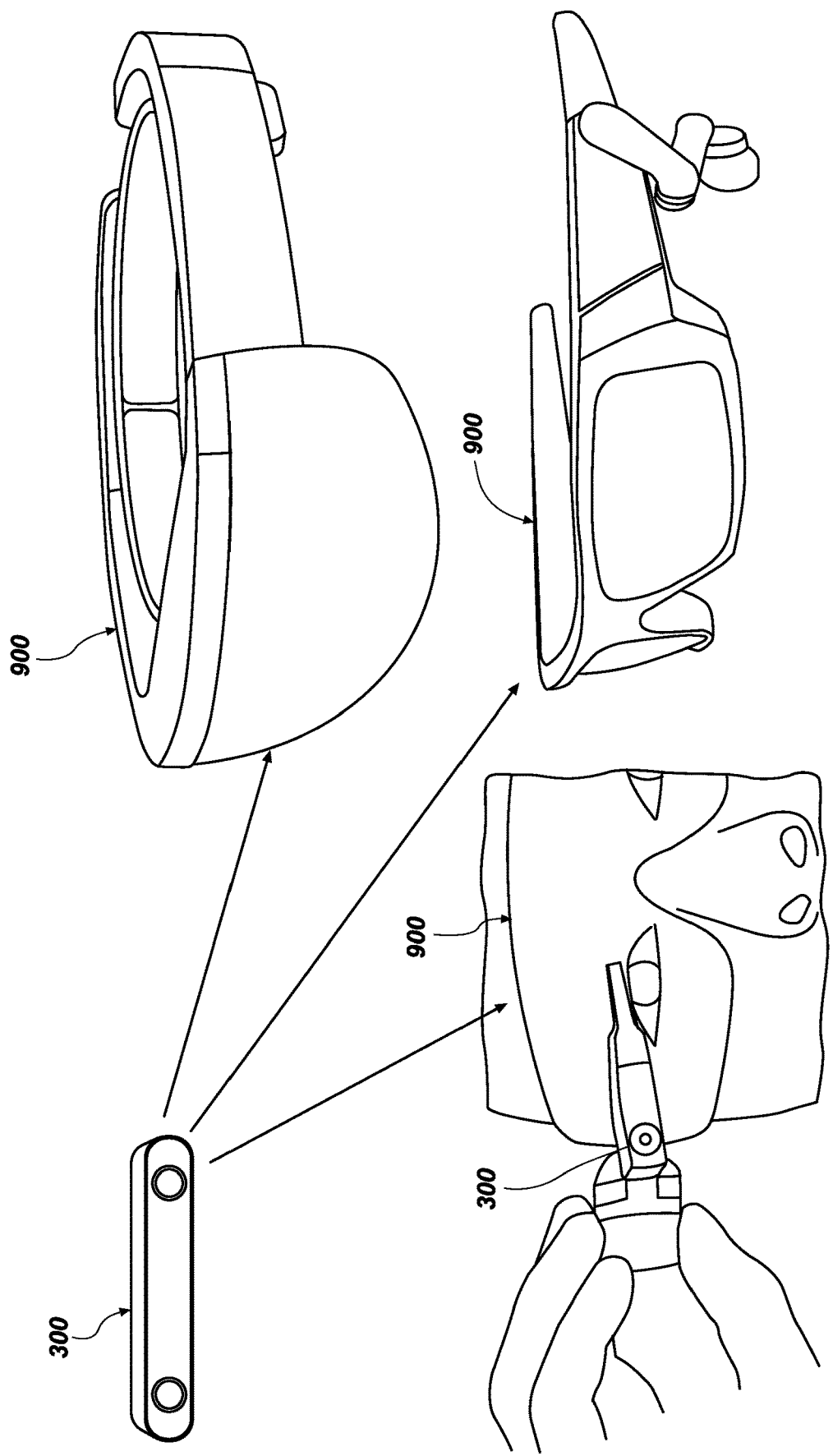
FIG. 5 is a perspective view of a 3D spatial mapping camera of another embodiment of the present disclosure.

In another embodiment, as shown in FIG. 5, the 3D spatial mapping camera 300 may be sized and configured to be fixed or removably attached to a headset 900. The headset 900 may be worn on the head of a user as part of eye protection or glasses or as part of a mixed reality headset.

Figure 6:
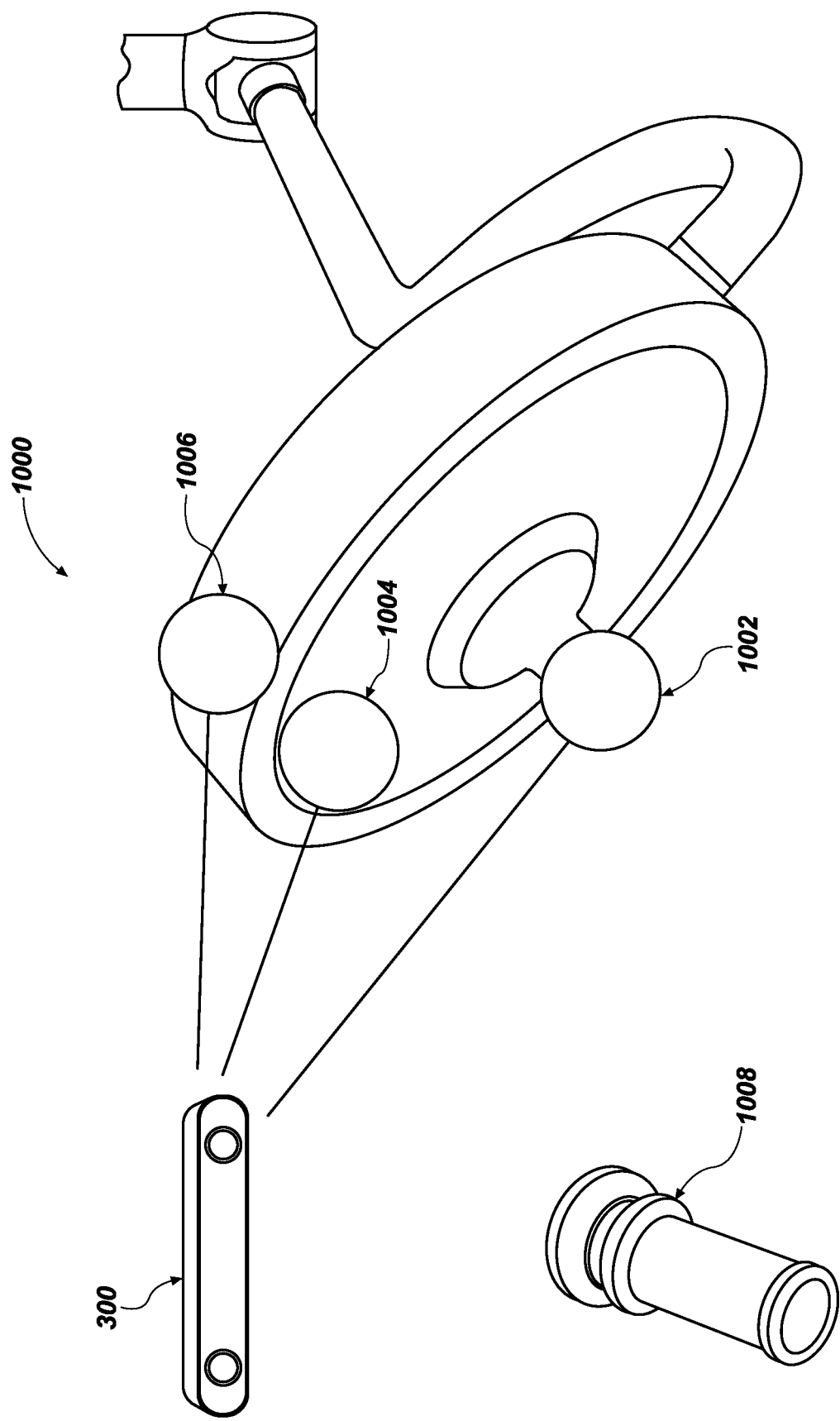
FIG. 6 is a perspective view of a 3D spatial mapping camera of another embodiment of the present disclosure.

In another embodiment, as shown in FIG. 6, the 3D spatial mapping camera 300 may be sized and configured to be attached or integrated into a light source panel 1000 used during an operation. The illustration of FIG. 6 shows different locations on the light source panel 1000 that could incorporate the 3D spatial mapping camera 300 (various location identified by the arrows). For example, the 3D spatial mapping camera may be incorporated into a handle 1002, a light source 1004, a frame 1006, or a sleeve 108 which may provide a sterile barrier for the handle 1002.

Figure 7:
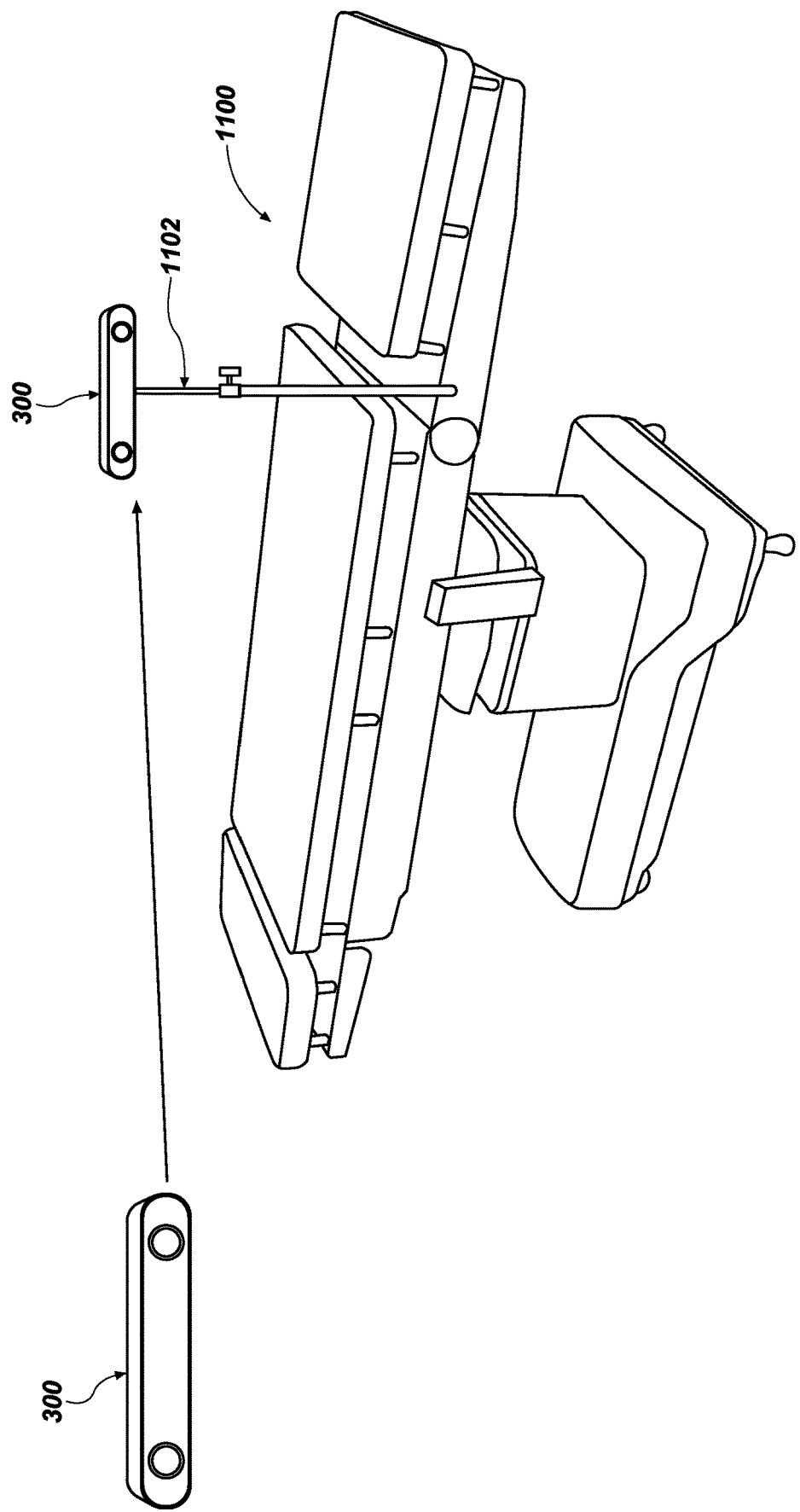
FIG. 7 is a perspective view of a 3D spatial mapping camera of another embodiment of the present disclosure.

In another embodiment, as shown in FIG. 7, the 3D spatial mapping camera 300 may be fixed or removably attached to an operating table 1100 via a mount 1102. The mount 1102 may be fixed or attached to the operating table at any desired location and may be adjustable in height and/or direction, enabling a surgeon or user to manipulate the angle of view and location of the 3D spatial mapping camera 300.

Figure 8:
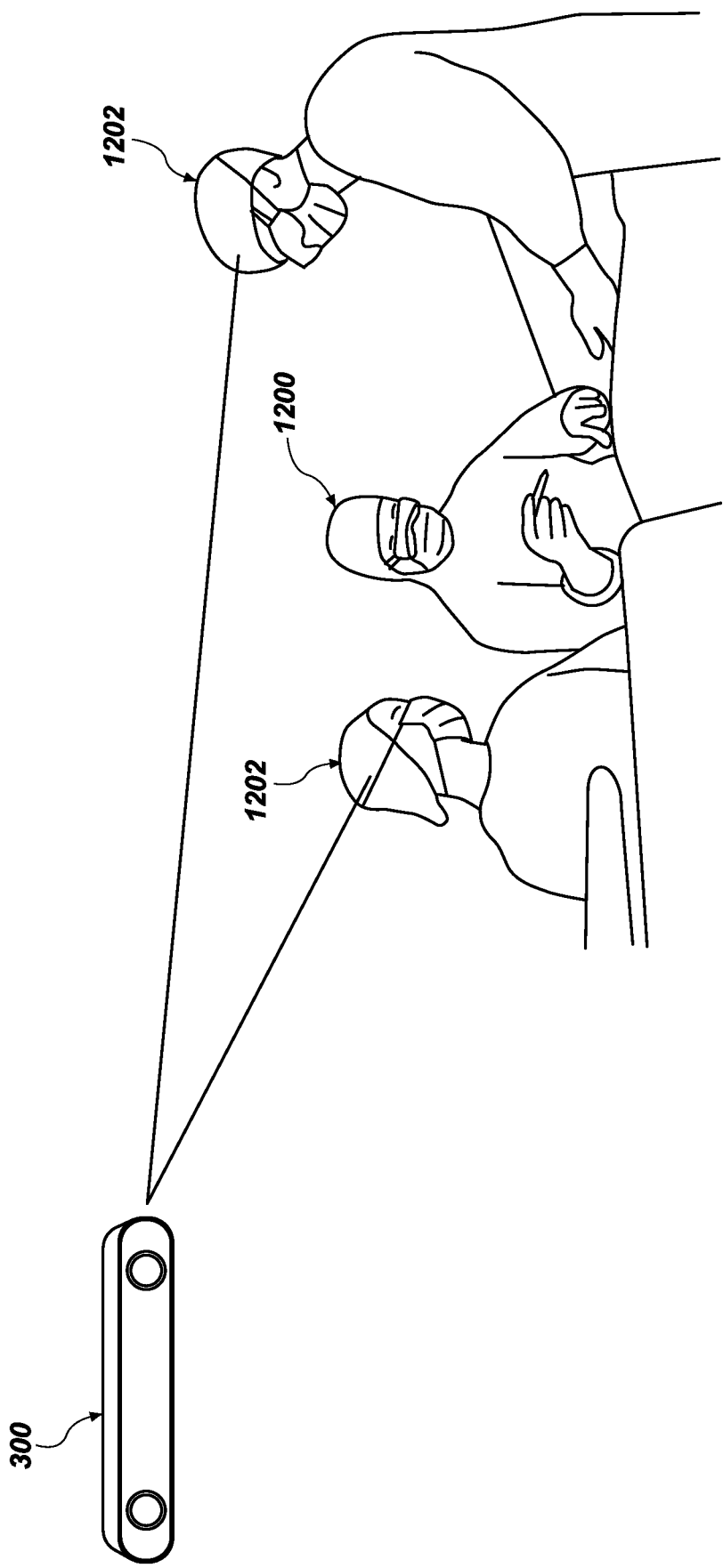
FIG. 8 is a perspective view of a 3D spatial mapping camera of another embodiment of the present disclosure.

In another embodiment, as shown in FIG. 8, the 3D spatial mapping camera 300 may be worn by a surgeon 1200 or an assistant 1202 using any of the aforementioned 3D spatial mapping camera embodiments. The 3D spatial mapping camera may be worn by a user inside or outside of a sterile field and could be worn in a way that would conform to specific procedural requirements a particular surgery.

Figure 9:
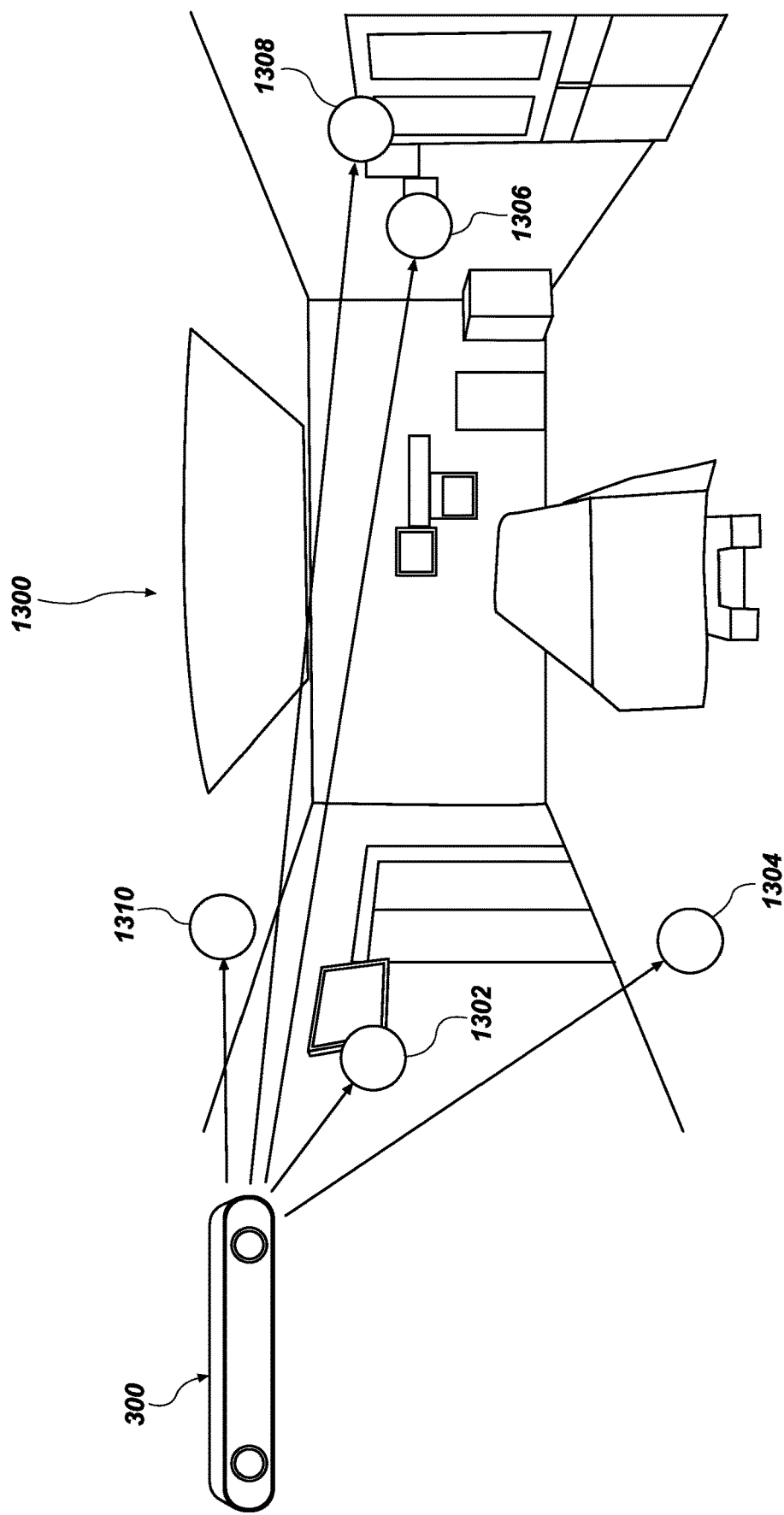
FIG. 9 is a perspective view of a 3D spatial mapping camera of another embodiment of the present disclosure.

In another embodiment, as shown in FIG. 9, the 3D spatial mapping camera 300 may be fixed or removably attached to a variety of different locations within an operating room 1300. For example, the 3D spatial mapping camera 300 may be attached or fixed to a wall 1302, a floor 1304, a wall panel 1306, a wall fixture 1308, a ceiling 1310 or any other desired location. Additionally, multiple 3D spatial mapping cameras 300 can be used simultaneously or in concert with one another where each 3D spatial mapping camera 300 may be mounted in different locations in the operating room 1300 or at the same location.

Figure 10:
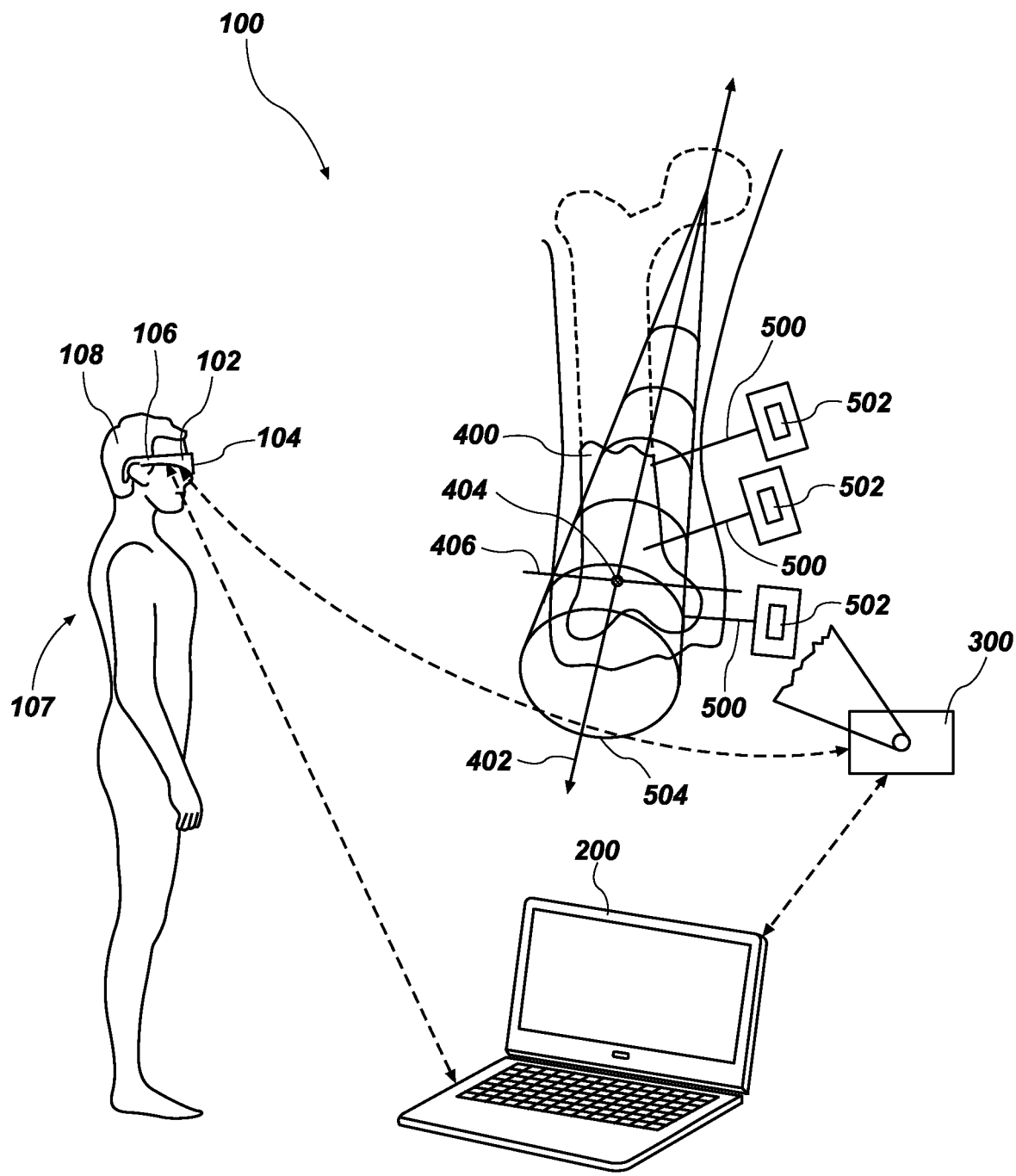
FIG. 10 is a perspective view of another embodiment system of the present disclosure.

In another embodiment, as shown in FIG. 10, the system 100 may include all of the same components as discuss and disclosed in FIG. 1, but may also include a plurality of markers 500 attached to the exposed portion of the bone 400. As disclosed above with respect to a single marker 500, the use of multiple markers 500 may provide additional data that may be captured by the 3D spatial mapping camera 300 and processed by the computer system 200 to locate the mechanical axis 402, mechanical center 404, and/or the cut line or plane 406.

Figure 11:
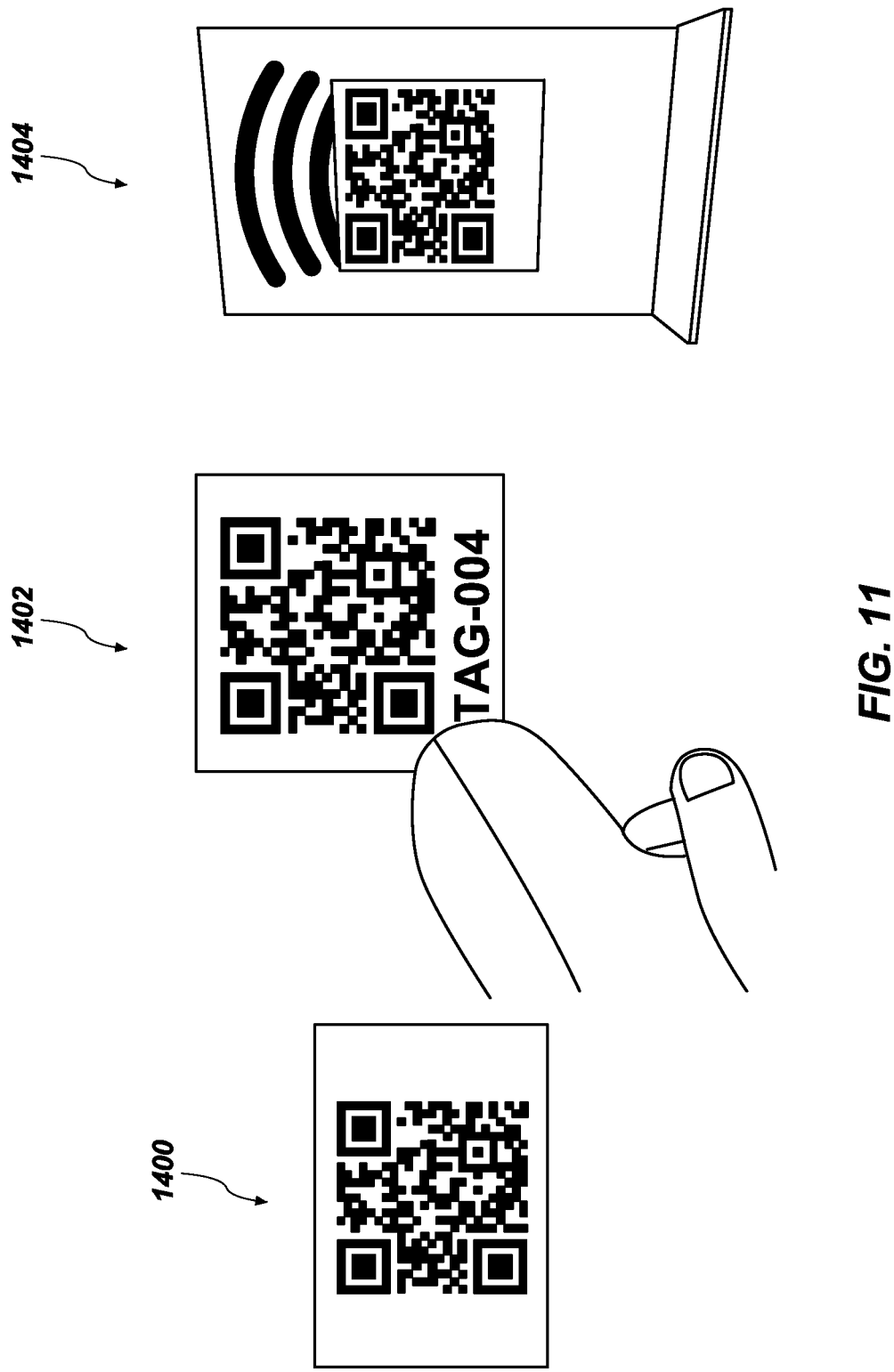
FIG. 11 is a perspective view of an optical label of another embodiment of the present disclosure.

In another embodiment, as shown in FIG. 11, the earlier disclosed optical labels 502 may be QR codes, as shown in examples 1400, 1402, and 1404. QR codes 1400, 1402, and 1404 may include various shapes and be of various desired sizes, and may include a plurality of corners, or sharp points that may be scanned their images captured by the 3D spatial mapping camera 300 to provide additional location data that may be processed by the computer system 200 as discussed in the other disclosed embodiments. Additionally, the markers 500 and/or optical labels 502 may be may of reflective material, of any desired color, may emit light, may be formed of any desired shape or of any desired size, to facilitate the capturing of an image to provide location data.

Figure 12:
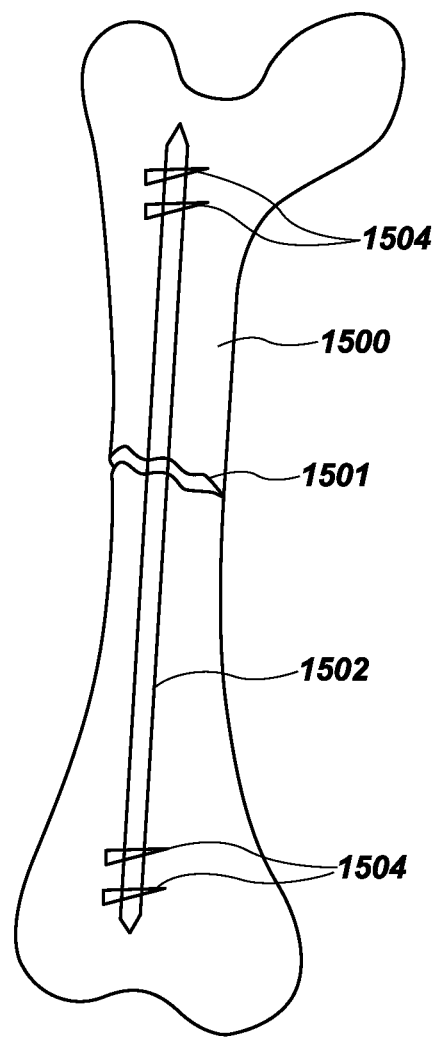
FIG. 12 is a perspective view of another embodiment of the present disclosure.

FIG. 12 illustrates that, additional uses of the disclosed system 100 and accompanying embodiments, may include a bone 1500 having a fracture 1501. By using the above-mentioned system and method a surgeon may identify the location of the fracture 1501, being a fulcrum or pivot point as described above, or other discontinuity. The system 100 can then be used, using the same location determining methodology and system described above, to locate the location of a stabilizing rod 1502 and the corresponding location of where screws 1504 would need to be located to be properly and accurately received by the rod 1502. This can be particularly useful in circumstances where critical locations are not visibly exposed to the surgeon.

It is to be understood that the various embodiments disclosed and described above and shown in the accompanying figures, may be interchangeably used together, independently or in any desired combination of disclosed features.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements, including but not limited to combinations of elements and/or features from the various disclosed embodiments may be devised by those skilled in the art without departing from the spirit and scope of the present disclosure and the invention is intended to cover such modifications, arrangements and combinations. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed:

1. A system for determining a location for a surgical procedure, utilizing:
    a 3D spatial mapping device, wherein the 3D spatial mapping device is configured to generate map data representative of a three dimensional map a surface of a bone,
    a marker configured to be attached to a distal end portion of the bone;
    wherein the 3D spatial mapping device is configured to capture a plurality of images of the marker as the bone is rotated in a non-linear path, wherein the images include marker data that identifies a marker location of the marker relative to the three dimensional map data of the surface of the bone;
    a computer system that receives the map data and marker data from the images captured by the 3D spatial mapping device and determines a position and orientation of a mechanical axis of the bone relative to the bone;
    a mixed reality display, wherein the computer system is configured to send the position and orientation of the mechanical axis to the mixed reality display and the mixed reality display is configured to provide a virtual image of the mechanical axis of the bone that visually appears to overlay the bone at the position and in the orientation of the mechanical axis when viewed with the mixed reality display.

2. The system of claim 1, wherein the mixed reality display is a mixed reality headset.

3. The system of claim 1, wherein the distal end section of the bone is visually exposed.

4. The system of claim 1, wherein the marker includes a QR code.

5. The system of claim 1, wherein the system includes only a single marker.

6. The system of claim 1, wherein the computer system that receives the data from the images captured by the 3D spatial mapping device and determines a location of a mechanical center of a head of the bone.

7. The system of claim 1, wherein the computer system that receives the data from the images captured by the 3D spatial mapping device and determines a location of a cut line or cut plane.

8. The system of claim 1, wherein the 3D spatial mapping device is configured to capture a plurality of images of the marker as the bone is rotated in a non-linear path about a pivot point, or fulcrum, that is not visual exposed.

9. The system of claim 1, wherein the system may include a plurality of markers attached to the bone.

10. The system of claim 1, wherein the 3D spatial mapping device is configured to capture the plurality of images at predetermined time intervals during rotation of the bone.

11. A system determining a location for a surgical procedure, comprising:
a 3D spatial mapping device, wherein the 3D spatial mapping device is configured to map a surface of a bone,
a marker, comprised of a QR code, attached to a distal end portion of the bone; wherein the 3D spatial mapping device is configured to capture a plurality of images of the marker relative to the bone as the bone moved relative to the 3D spatial mapping device, wherein the images include marker data that identifies a location of the marker relative to the bone;
a computer system that receives the marker data from the images captured by the 3D spatial mapping device and determines a position and orientation of a mechanical axis of the bone relative to the bone;
a mixed reality display, wherein the computer system is configured to send the position and orientation of the mechanical axis relative to the bone to the mixed reality display and the mixed reality display is configured to provide a virtual image of the mechanical axis of the bone that visually appears to overlay the bone at the position and in the orientation of the mechanical axis when viewed with the mixed reality display.

12. The system of claim 11, wherein the mixed reality display is a mixed reality headset.

13. The system of claim 11, wherein the distal end section of the bone is visually exposed.

14. The system of claim 11, wherein the movement of the bone occurs along a non-linear path.

15. The system of claim 11, wherein the system includes only a single marker.

16. The system of claim 11, wherein the computer system that receives the data from the images captured by the 3D spatial mapping device and determines a location of a mechanical center of a head of the bone.

17. The system of claim 11, wherein the computer system that receives the data from the images captured by the 3D spatial mapping device and determines a location of a cut line or cut plane.

18. The system of claim 11, wherein the 3D spatial mapping device is configured to capture a plurality of images of the marker as the bone is rotated in a non-linear path about a pivot point, or fulcrum, that is not visual exposed.

19. The system of claim 11, wherein the system may include a plurality of markers attached to the bone.

20. The system of claim 11, wherein the 3D spatial mapping device is configured to capture the plurality of images at predetermined time intervals during rotation of the bone.

21. A system for determining a location for a surgical procedure, utilizing:
a 3D spatial mapping camera, wherein the 3D spatial mapping camera is configured to map a bone,
a marker attached to a distal end section of the bone;
wherein the 3D spatial mapping camera is configured to capture a plurality of images of the marker as the bone is moved, wherein the images include data that identifies a location of the marker;
a computer system that receives the data from the images captured by the 3D spatial mapping camera and determines a location of a mechanical axis of the bone; and
a mixed reality display, wherein the computer system is configured to send the location of the mechanical axis to the mixed reality display and the mixed reality display is configured to provide a virtual image of the mechanical axis that visually appears to overlay the bone at a position and in an orientation relative to the bone when viewed with the mixed reality display.

22. The system of claim 21, wherein the mixed reality display is a mixed reality headset.

23. The system of claim 21, wherein the distal end section of the bone is visually exposed.

24. The system of claim 21, wherein the marker includes a QR code.

25. The system of claim 21, wherein the system includes only a single marker.

26. The system of claim 21, wherein the computer system that receives the data from the images captured by the 3D spatial mapping camera and determines a location of a mechanical center of a head of the bone.

27. The system of claim 21, wherein the computer system that receives the data from the images captured by the 3D spatial mapping camera and determines a location of a mechanical axis of the bone.

28. The system of claim 21, wherein the 3D spatial mapping camera is configured to capture a plurality of images of the marker as the bone is rotated in a non-linear path about a pivot point, or fulcrum, that is not visual exposed.

29. The system of claim 21, wherein the system may include a plurality of markers attached to the bone.

30. A system for determining a location for a surgical procedure, utilizing:
a 3D spatial mapping camera, wherein the 3D spatial mapping camera is configured to map a bone,
a single marker having a QR code attached to a distal end section of the bone, wherein the distal end section of the bone is visually exposed;
wherein the 3D spatial mapping camera is configured to capture a plurality of images of the marker as the bone is rotated in a non-linear path about a pivot point, or fulcrum, that is not visual exposed, wherein the images include data that identifies a location of the marker, and wherein the 3D spatial mapping camera is configured to capture the plurality of images at predetermined time intervals during rotation of the bone;
a computer system that receives the data from the images captured by the 3D spatial mapping camera and determines a location of a cut plane on the bone; and
a mixed reality display, the mixed reality display being a mixed reality headset, wherein the computer system is configured to send the location of the mechanical axis to the mixed reality display and the mixed reality display is configured to provide a virtual display of the mechanical axis of the bone, and wherein the computer system also determines a location of a mechanical center of a head of the bone.

* * * * *